United States Patent
Block et al.

(10) Patent No.: US 8,361,128 B2
(45) Date of Patent: Jan. 29, 2013

(54) METHOD AND APPARATUS FOR PERFORMING A COMPUTER-ASSISTED ORTHOPAEDIC PROCEDURE

(75) Inventors: D. Steven Block, Warsaw, IN (US); Thorsten M. Burger, Munich (DE); Francois Urvoy, Munich (DE); Magnus E. Flett, West Yorkshire (GB); Michal Slomczykowski, Harrogate (GB); Marcellino Maheson, Wales (GB); Roger Oakeshott, Stepney (AU); Alec Birkbeck, Leeds (GB)

(73) Assignees: DePuy Products, Inc., Warsaw, IN (US); DePuy International Limited (GB)

( * ) Notice: Subject to any disclaimer, the term of this patent is extended or adjusted under 35 U.S.C. 154(b) by 2630 days.

(21) Appl. No.: 10/956,181

(22) Filed: Sep. 30, 2004

(65) Prior Publication Data
US 2006/0084890 A1   Apr. 20, 2006

(51) Int. Cl.
| A61B 17/04 | (2006.01) |
| A61B 17/86 | (2006.01) |
| A61B 17/58 | (2006.01) |
| A61B 17/60 | (2006.01) |
| A61F 2/08 | (2006.01) |
| A61F 2/00 | (2006.01) |

(52) U.S. Cl. .......................................... 606/304; 606/96
(58) Field of Classification Search ................ 606/73, 606/300, 304
See application file for complete search history.

(56) References Cited

U.S. PATENT DOCUMENTS

| 5,456,267 | A | 10/1995 | Stark |
| 5,520,694 | A | 5/1996 | Dance et al. |
| 5,628,315 | A | 5/1997 | Vilsmeier et al. |
| 5,643,268 | A | 7/1997 | Vilsmeier et al. |
| 5,702,406 | A | 12/1997 | Vilsmeier et al. |
| 5,769,861 | A | 6/1998 | Vilsmeier |
| 5,889,834 | A | 3/1999 | Vilsmeier et al. |
| 6,178,345 | B1 | 1/2001 | Vilsmeier et al. |
| 6,187,018 | B1 | 2/2001 | Sanjay-Gopal et al. |
| 6,203,543 | B1 * | 3/2001 | Glossop ..................... 606/60 |
| 6,210,376 | B1 * | 4/2001 | Grayson ..................... 604/264 |
| 6,223,067 | B1 | 4/2001 | Vilsmeier et al. |
| 6,226,548 | B1 * | 5/2001 | Foley et al. ................. 600/426 |
| 6,351,659 | B1 | 2/2002 | Vilsmeier |
| 6,424,856 | B1 | 7/2002 | Vilsmeier et al. |
| 6,428,547 | B1 | 8/2002 | Vilsmeier et al. |
| 6,434,507 | B1 | 8/2002 | Clayton et al. |

(Continued)

FOREIGN PATENT DOCUMENTS

| EP | 1281365 A1 | 2/2003 |
| JP | 57156753 | 9/1982 |

(Continued)

OTHER PUBLICATIONS

European Search Report for European Application No. 05255807.9-2318, Dec. 22, 2005, 3 pgs.

(Continued)

*Primary Examiner* — Kevin T Truong
*Assistant Examiner* — David Bates
(74) *Attorney, Agent, or Firm* — Barnes & Thornburg LLP

(57) ABSTRACT

A method of performing a computer-assisted orthopaedic procedure includes securing a sensor support instrument to the patient's bone. A number of sensors are secured to the support instrument. A computer-assisted orthopaedic surgical instrument is also disclosed.

7 Claims, 2 Drawing Sheets

U.S. PATENT DOCUMENTS

| | | | |
|---|---|---|---|
| 6,514,259 B2 | 2/2003 | Picard et al. | |
| 6,719,757 B2 * | 4/2004 | Neubauer et al. | 606/53 |
| 6,856,828 B2 * | 2/2005 | Cossette et al. | 600/429 |
| 7,458,977 B2 | 12/2008 | McGinley et al. | |
| 2001/0034530 A1 | 10/2001 | Malackowski et al. | |
| 2002/0038118 A1 | 3/2002 | Shoham | |
| 2002/0077540 A1 * | 6/2002 | Kienzle, III | 600/424 |
| 2002/0107518 A1 | 8/2002 | Neubauer et al. | |
| 2003/0078565 A1 * | 4/2003 | Vilsmeier et al. | 606/1 |
| 2003/0153829 A1 | 8/2003 | Sarin et al. | |
| 2003/0153978 A1 | 8/2003 | Whiteside | |
| 2004/0153062 A1 | 8/2004 | McGinley et al. | |
| 2005/0171551 A1 * | 8/2005 | Sukovich et al. | 606/86 |
| 2006/0025775 A1 | 2/2006 | Malkani | |
| 2006/0069324 A1 | 3/2006 | Block et al. | |

FOREIGN PATENT DOCUMENTS

| | | |
|---|---|---|
| WO | WO 01/64124 A1 | 9/2001 |
| WO | WO 2004/030557 A1 | 4/2004 |

OTHER PUBLICATIONS

Japanese Search Report, Japanese Patent Application No. 2005-284785, Aug. 16, 2011, 4 pages.

European Search report for European Patent Application No. 05255807.9-1526, Jul. 1, 2009, 4 pages.

Australian Search Report for Australian Patent Application No. 2005205808; May 26, 2010; 3 pgs.

* cited by examiner

METHOD AND APPARATUS FOR PERFORMING A COMPUTER-ASSISTED ORTHOPAEDIC PROCEDURE

FIELD OF THE DISCLOSURE

The present disclosure relates generally to a computer-assisted surgical instrument for use in the performance of an orthopaedic procedure.

BACKGROUND

Many computer guided orthopaedic surgical procedures are based on determining the position of bones, and relating this position to the computer via some type of ultrasonic, magnetic resonance, or optical sensor. In such cases, a first sensor may be secured to the patient's bone, with a second sensor being secured to the surgical instrument so that the instrument may be subsequently guided via a computer into the desired position within the patient's bone. U.S. Patents and Patent Publications relating to computer guided surgery include U.S. Pat. No. 5,520,694 and U.S. Patent Application Publication Nos. 2003/0153978 A1 and 2003/01538829 A1, each of which is hereby incorporated by reference. Similar computer-assisted navigation systems are disclosed in U.S. Pat. Nos. 6,514,259; 6,434,507; 6,428,547; 6,424,856; 6,351,659; 6,223,067; 6,187,018; 6,178,345; 5,889,834; 5,769,861; 5,702,406; 5,643,268; and 5,628,315, along with U.S. Patent Application Publication No. 2002/0038118 A1, each of which is hereby incorporated by reference.

SUMMARY

According to one aspect of the disclosure, a method of performing a computer-assisted orthopaedic hip procedure includes securing a sensor support instrument to the lesser trochanter of the patient's femur. The sensor support instrument has a number of sensors secured thereto.

In one exemplary implementation, the sensor support instrument includes a screw that is screwed into the lesser trochanter. The screw may be a Schanz screw. The screw may be cannulated. The screw may be a cannulated Schanz screw.

The sensor support instrument may also include a sensor support having a number of support arms. Each of the support arms may have a sensor secured thereto.

The sensor support instrument may also include a support sleeve through which the screw extends.

According to another aspect of the disclosure, a method of performing a computer-assisted orthopaedic procedure includes securing a cannulated screw to a patient's bone. A sensor may be secured to the cannulated screw.

The tip of the cannulated screw may be positioned in the medullary canal of the patient's bone. The other end of the cannulated screw is positioned outside of the patient's body.

The cannulated screw may be coupled to a negative pressure source via a suction tube thereby placing the medullary canal of the patient's bone in fluid communication with the negative pressure source.

According to another aspect of the disclosure, a computer-assisted orthopaedic surgical instrument includes a cannulated screw having a sensor support coupled thereto. A number of sensors may be secured to the sensor support.

The sensor support may be configured with a number of support arms. Each of the support arms may have a sensor secured thereto.

The surgical instrument may also include a support sleeve through which the cannulated screw extends.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DRAWINGS

Figure 1:
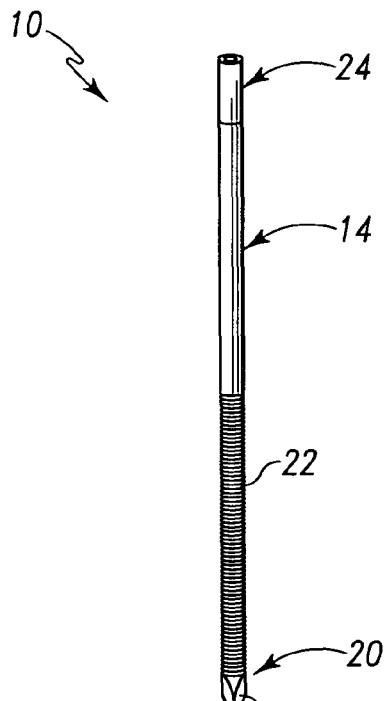
FIG. 1 is an exploded perspective view of the cannulated screw and the sensor support sleeve.
Figure 1:
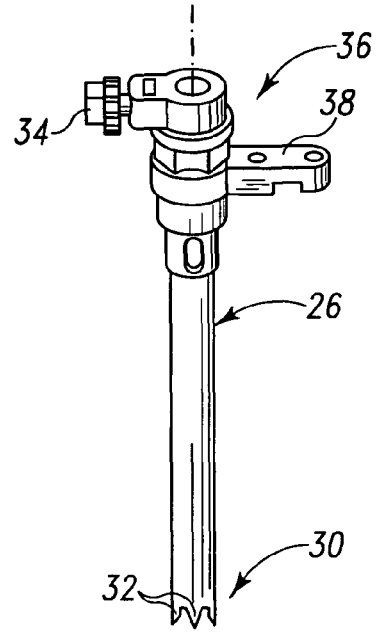
Figure 2:
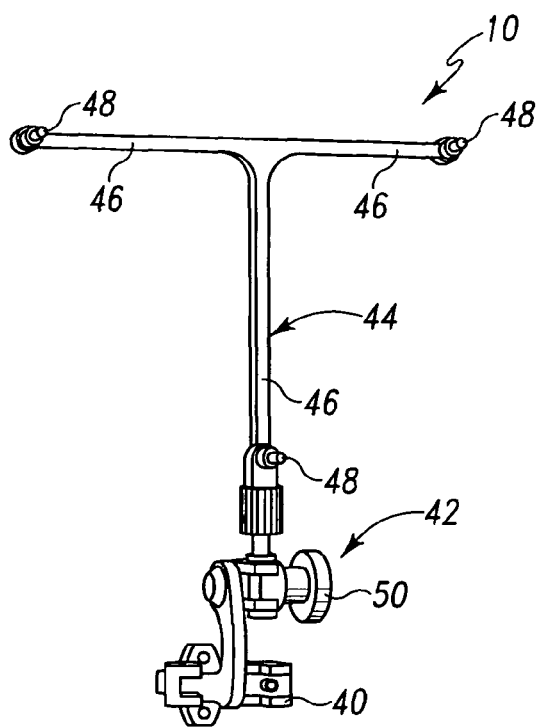
FIG. 2 is a perspective view of the sensor support and the adjustable linkage.
Figure 3:
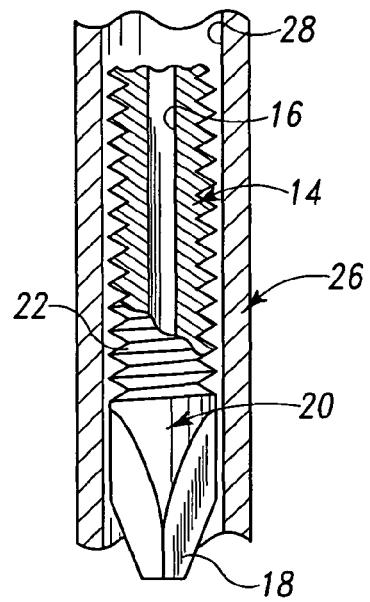
FIG. 3 is a fragmentary cross sectional view showing the cannulated screw positioned in the sensor support sleeve.

Referring now to FIGS. 1-3, there is shown a surgical instrument 10 for use in a computer-assisted orthopaedic procedure. The surgical instrument 10 is used to support a number of sensors 12 (see FIG. 4). The location of the sensors 12 is tracked or otherwise monitored by a computer (not shown) of a computer-assisted surgical system. The sensors 12 may be embodied as ultrasonic, magnetic resonance, or optical sensors, for example. Sensors which are suitable for use as the sensors 12 are commercially available from BrainLAB AG of Heimstetten, Germany.

The surgical instrument 10 includes a screw 14 which may be screwed into the patient's bone during a surgical procedure. In an exemplary implementation, the screw 14 is embodied as a Schanz screw. The screw 14 is cannulated, and, as such, has an elongated bore 16 extending therethrough. The cannulated screw 14 has a trocar tip 18 defined in one end portion 20 thereof. Other tip configurations, such as a self-tapping drill bit tip, may also be used. A series of threads 22 extend from the tip 18 in the direction toward the other end portion 24 of the screw 14.

The surgical instrument 10 also includes a sensor support sleeve 26. The sensor support sleeve 26 has an elongated bore 28 extending therethrough. One end 30 of the sensor support sleeve 26 has a number of bone engaging tips 32 defined therein which engage the outer surface of the patient's bone. A set screw 34 is located on the other end 36 of the sensor support sleeve 26. When tightened, the set screw 34 engages the cannulated screw 14 thereby preventing relative rotation between the screw 14 and the support sleeve 26.

A mounting flange 38 extends outwardly from the outer end 36 of the sensor support sleeve 26. A corresponding mounting flange 40 of an adjustable linkage 42 is removably coupled to the sleeve's mounting flange 38. The linkage 42 couples the support sleeve 26 to a sensor support 44. The sensor support 44 includes three support arms 46, each of which has a threaded shaft 48 extending outwardly therefrom. Illustratively, each of the sensors 12 has a threaded bore (not shown) formed therein. The sensors are threaded onto the shafts 48 of the support arms 46. Although the sensor support 44 is herein described as having three support arms 46 (for supporting three sensors 12), it should be appreciated that the sensor support 44 may be configured with any number of support arms 46 (to support any number of sensors 12). Further, it should be appreciated that although each support arm 46 of the sensor support 44 includes a threaded shaft 48 and each sensor 12 includes a threaded bore for attachment onto one of the threaded shafts 48, the sensors 12 may include non-threaded bores and may be snap-fit or press-fit onto non-threaded shafts or posts (not shown) of each support arm 46.

The adjustable linkage 42 includes a tensioning knob 50. By loosening the knob 50, the sensor support 44 may be pivoted or otherwise moved relative to the sensor support sleeve 26 thereby allowing a surgeon to adjust the position of the sensors 12. Once the surgeon has positioned the sensor support 44 in a desired position, the knob 50 may be tightened thereby retaining the support 44 in such a position.

Figure 4:
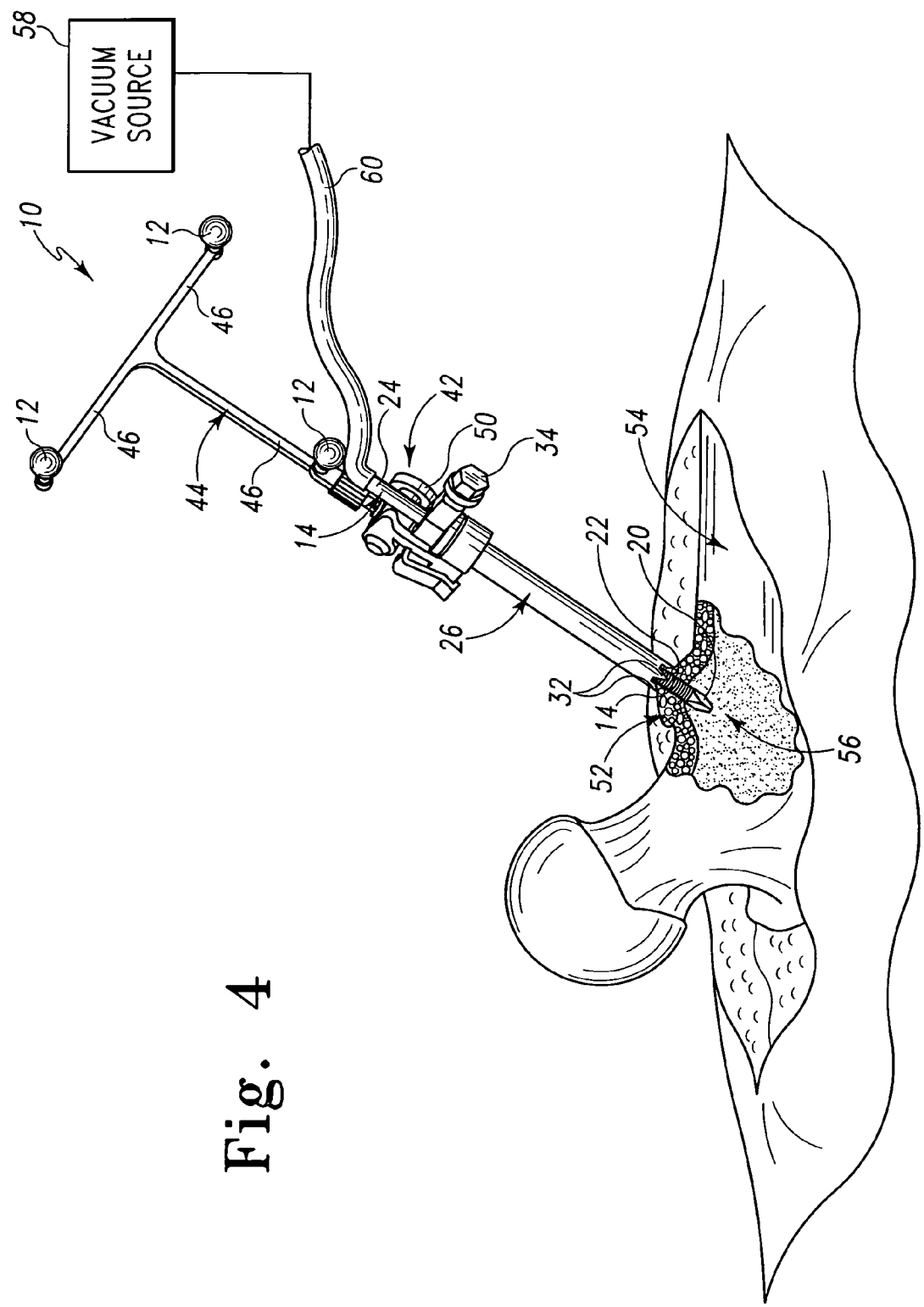
FIG. 4 is a fragmentary perspective view showing the sensor support instrument of FIGS. 1-3 secured to the lesser trochanter of a patient's femur.

Use of the surgical instrument 10 is shown in FIG. 4, and will now be described in greater detail in regard to an orthopaedic hip replacement procedure. However, it should be appreciated that use of the surgical instrument 10 is not limited to hip procedures, with the following discussion being exemplary in nature.

As shown in FIG. 4, the surgical instrument 10 is secured to the lesser trochanter 52 of the patient's femur 54. The lesser trochanter 52 provides a convenient anatomical landmark which is readily accessible during most hip procedures. It allows the sensors 12 to be positioned in a desirable location with respect to the surgeon and the computer/camera/detector of the computer-assisted surgical system (not shown).

The cannulated screw 14 is advanced through the lesser trochanter 52 such that its tip 18 extends into the medullary canal 56 of the patient's femur 54. The outer end portion 24 of the cannulated screw 14 extends out of the patient's body. The cannulated screw 14 may be inserted in any desirable angle. By inserting the cannulated screw 14 into the femur 54, a fluid path for venting the proximal femur is created. Such venting of the proximal femur removes blood, fat, intramedullary marrow, or other substances which could be the source of embolic material during, for example, the preparation and cementation process.

Moreover, a negative pressure source, such as a vacuum source 58 may be fluidly coupled to the outer end 24 of the cannulated screw 14 via a suction tube 60. In such a way, the intramedullary canal 56 of the patient's femur 54 is placed in fluid communication with the vacuum source 58 via a fluid path that includes the elongated bore 16 of the cannulated screw 14 and the suction tube 60. Use of the vacuum source 58 facilitates venting of the proximal femur. Moreover, during cementation, the negative pressure assists interdigitation of the bone cement to the bone surface. The negative pressure also helps draw down the femoral component (e.g., femoral articular surface component) thereby reducing the need for impaction.

The sensor support sleeve 26 is then advanced over the cannulated screw 14 such that the screw 14 is received into the elongated bore 28 of the sleeve 26. The support sleeve 26 is advanced to a position in which its tips 32 engage the outer surface of the patient's femur 54. If need be, the rotational position of the support sleeve 26 relative to the screw 14 may then (or at anytime) be adjusted by loosening the set screw 34 and thereafter rotating the sleeve relative to the screw 14. Once the sleeve 26 is positioned in a desired rotational position relative to the screw 14, the set screw 34 is tightened thereby preventing relative rotation between the screw 14 and the support sleeve 26.

If not already installed (e.g., prior to installation of the support sleeve 26), the adjustable linkage 42 (and hence the sensor support 44) is then secured to the sensor support sleeve 26. To do so, the mounting flange 38 of the sensor support sleeve 26 is mated with or otherwise secured to the corresponding mounting flange 40 of the adjustable linkage 42. If not already installed, the sensors 12 are then installed onto the threaded shafts 48 of the support arms 46. The location of the sensors 12 may then be adjusted (if need be) by use of the adjustment knob 50 (to pivot the sensor support 44) and/or the set screw 34 (to rotate the support sleeve 26 and hence the sensor support 44).

Once the sensors 12 are in place, the computer-assisted orthopaedic hip procedure may continue. During the conclusion of the procedure, the support sleeve 26 (with or without the adjustment linkage 42 having been previously removed) is removed from the patient, and the cannulated screw 14 is reversed out of the patient's femur 54.

Although the sensor support 44 and the sensor support sleeve 26 are shown as two separate components, as shown in FIGS. 1 and 2, which may be secured to one another, as shown in FIG. 4, it should be appreciated that the sensor support 44 and the sensor support sleeve 26 may form a common, one-piece component or may still be embodied as multiple components which are not removable from one another.

It should be appreciated that the lesser trochanter 52 may be used as an insertion site for any type of sensor support instrument. In particular, although insertion into the lesser trochanter 52 is herein described in regard to the surgical instrument 10, it is contemplated that the lesser trochanter 52 may serve as a beneficial insertion site for any type of instrument for supporting the sensors 12. It is also contemplated that the surgical instrument 10 may be inserted into bone sites other than the lesser trochanter (including sites on bones other than the femur).

While it is described that the sensor support instrument 26 is secured to the lesser trochanter 52, it is contemplated that the lesser trochanter 52 may serve as an anatomical landmark or location for allowing the surgical team to measure and position the sensor support instrument 26 a particular distance in any direction from the lesser trochanter 52. In other words, it is contemplated that the computer-assisted hip surgery may include locating the lesser trochanter 52 and then positioning the sensor support instrument 26 some distance in any direction from the lesser trochanter 52 (i.e., but not on the lesser trochanter 52 itself). Once the sensor support instrument 26 is secured to the patient's femur in the desired location, the sensor(s) 12 may be secured to the sensor support instrument 26 and the screw 14 may be inserted through the sensor support instrument 26 and screwed into the patient's bone.

While the disclosure is susceptible to various modifications and alternative forms, specific exemplary embodiments thereof have been shown by way of example in the drawings and has herein be described in detail. It should be understood, however, that there is no intent to limit the disclosure to the particular forms disclosed, but on the contrary, the intention is to cover all modifications, equivalents, and alternatives falling within the spirit and scope of the disclosure.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. A computer-assisted orthopaedic surgical instrument, comprising:
   a negative pressure source,
   a cannulated screw, wherein (i) the cannulated screw has a first end portion and a second end portion, (ii) the first end portion has a pointed tip defined therein and (iii) the second end portion is fluidly coupled to the negative pressure source, and
   a sensor support coupled to the cannulated screw.

2. The surgical instrument of claim 1, wherein:
   the sensor support comprises a number of support arms, and
   each of the sensor support arms is configured to support a sensor.

3. The surgical instrument of claim 1, wherein the cannulated screw comprises a cannulated Schanz screw.

4. The surgical instrument of claim 1, further comprising a support sleeve, wherein:
   the support sleeve defines an elongated bore, and
   the cannulated screw is positionable in the elongated bore.

5. The surgical instrument of claim 4, further comprising an adjustable linkage, wherein:
   a first portion of the adjustable linkage is securable to the support sleeve, and
   a second portion of the adjustable linkage is securable to the sensor support.

6. The surgical instrument of claim 4, wherein the sensor support is secured to the support sleeve.

7. The surgical instrument of claim 4, wherein the support sleeve comprises a set screw which is operable to engage the cannulated screw.

* * * * *